(12) United States Patent
McDonald

(10) Patent No.: US 12,714,454 B1
(45) Date of Patent: Aug. 25, 2026

(54) MULTICUT CARDIAC VALVE CUTTER

(71) Applicant: Michael B. McDonald, Cordova, TN (US)

(72) Inventor: Michael B. McDonald, Cordova, TN (US)

(73) Assignee: Bonaparte Medical, Inc., Cordova, TN (US)

( * ) Notice: Subject to any disclaimer, the term of this patent is extended or adjusted under 35 U.S.C. 154(b) by 448 days.

(21) Appl. No.: 18/114,481

(22) Filed: Feb. 27, 2023

Related U.S. Application Data

(60) Provisional application No. 63/313,947, filed on Feb. 25, 2022.

(51) Int. Cl.
*A61B 17/32* (2006.01)
*A61B 17/00* (2006.01)

(52) U.S. Cl.
CPC .................. *A61B 17/32002* (2013.01); *A61B 2017/00243* (2013.01); *A61B 2017/320052* (2013.01)

(58) Field of Classification Search
CPC .......... A61B 17/22097; A61B 17/3207; A61B 17/32075; A61B 17/320758; A61B 17/320783; A61B 2017/320024; A61B 2017/320032; A61B 2017/320052; A61B 2017/320733; A61B 2017/320741; A61B 2017/320775; A61B 2017/320766; A61B 2017/00783
See application file for complete search history.

(56) References Cited

U.S. PATENT DOCUMENTS

| | | | |
|---|---|---|---|
| 4,986,807 | A | 1/1991 | Farr |
| 4,994,067 | A | 2/1991 | Summers |
| 5,087,265 | A | 2/1992 | Summers |
| 5,092,873 | A | 3/1992 | Simpson et al. |
| 5,188,635 | A | 2/1993 | Radtke |
| 5,431,673 | A | 7/1995 | Summers |
| 5,584,842 | A | 12/1996 | Fogarty |

(Continued)

FOREIGN PATENT DOCUMENTS

| | | |
|---|---|---|
| WO | 8906935 | 8/1989 |

OTHER PUBLICATIONS

Extended European Search Report and Opinion issued Jun. 29, 2016 in related European Application No. 13861326.0 filed on Dec. 5, 2013.

(Continued)

*Primary Examiner* — Elizabeth Houston
*Assistant Examiner* — Lindsey Bachman
(74) *Attorney, Agent, or Firm* — Jake M. Gipson; Bradley Arant Boult Cummings LLP

(57) ABSTRACT

A cutting device is provided to cut stenosed aortic valve leaflets using a percutaneous approach. The device has a central catheter that moves over a guide wire to pass into a patient's aortic valve. Cutting wires are deployed from the catheter and have high speed rotating cutting surfaces that cut into the stenosed tissue. A plurality of guidewires outward from the cutting wires serve to center and position the cutter within the patient's aortic valve. In an alternative embodiment, a shield is deployed between the cutting wires and the patient's aortic valve to prevent the cutting wires from cutting into the aortic root or aortic sinus wall.

11 Claims, 3 Drawing Sheets

(56) References Cited

U.S. PATENT DOCUMENTS 5,766,192 A * 6/1998 Zacca ............ A61B 17/320725 606/198
5,910,150 A 6/1999 Saadat
6,936,024 B1 8/2005 Houser
7,534,242 B2 5/2009 Buehlmann
2003/0055444 A1* 3/2003 Evans ............ A61B 17/320725 606/159
2004/0204730 A1 10/2004 Goldberg et al.
2005/0187616 A1 8/2005 Realyvasquez
2007/0185513 A1 8/2007 Woolfson et al.
2008/0004646 A1 1/2008 To et al.
2014/0358123 A1* 12/2014 Ueda ....................... A61F 2/958 604/510
2019/0069921 A1* 3/2019 Samuels ........ A61B 17/320725

OTHER PUBLICATIONS

International Search Report and Written Opinion mailed Mar. 10, 2014 in corresponding International Application No. PCT/US2013/073356 filed Dec. 5, 2013.

* cited by examiner

MULTICUT CARDIAC VALVE CUTTER

REFERENCE TO RELATED APPLICATIONS

This application claims priority to Provisional Patent Application U.S. Ser. No. 63/313,947, entitled "Multicut Cardiac Valve Cutter" and filed on Feb. 25, 2022, which is fully incorporated herein by reference.

BACKGROUND AND SUMMARY

Aortic stenosis, an abnormal narrowing of the aortic valve, is the most common valve disease in the world. Patients with aortic stenosis experience restricted blood flow from the heart and suffer increased risk of heart failure. Currently available treatments for aortic stenosis include surgical valve replacement, transcatheter valve replacement, and balloon aortic valvuloplasty. In surgical valve replacement, the patient undergoes open heart surgery to replace the stenotic valve. A transcatheter valve replacement (TAVR), in which the valve is replaced in a transcatheter procedure, is a less invasive approach to replacing the stenotic valve. Balloon aortic valvuloplasty does not replace the valve, but rather a balloon catheter is inflated within the aortic valve to increase the size of the opening.

Each of these existing treatments has advantages and drawbacks. The drawbacks of the surgical approach include the obvious risks of such major surgery. Drawbacks of the TAVR and balloon aortic valvuloplasty include having the heart undergo short and rapid ventricular pacing during portions of the procedure and risks inherent in implementation of a foreign device into the heart. Further, the costs of the surgical valve replacement and TAVR are quite high. The balloon aortic valvuloplasty produces improvements in the aortic stenosis, but the improvements typically last only a few months. What is desired is a lower cost, safer minimally-invasive procedure to increase the opening of a stenotic valve. Previous devices designed for meeting this need include those disclosed in U.S. Pat. No. 10,864,009, titled "Valve Cutter," and U.S. Pat. No. 9,468,458, titled "Aortic Valve Cutter."

A cardiac valve cutter of the present disclosure makes cuts in cardiac valves from a percutaneous approach. The device has a central catheter that moves over a guide wire to pass into a patient's aortic valve. Cutting wires are deployed from the catheter and have high speed rotating cutting surfaces that cut into the stenosed tissue. A plurality of guidewires outward from the cutting wires serve to center and position the cutter within the patient's aortic valve. In an alternative embodiment, a shield is deployed between the cutting wires and the patient's aortic valve to prevent the cutting wires from cutting into the aortic root or aortic sinus wall.

DETAILED DESCRIPTION

Figure 1:
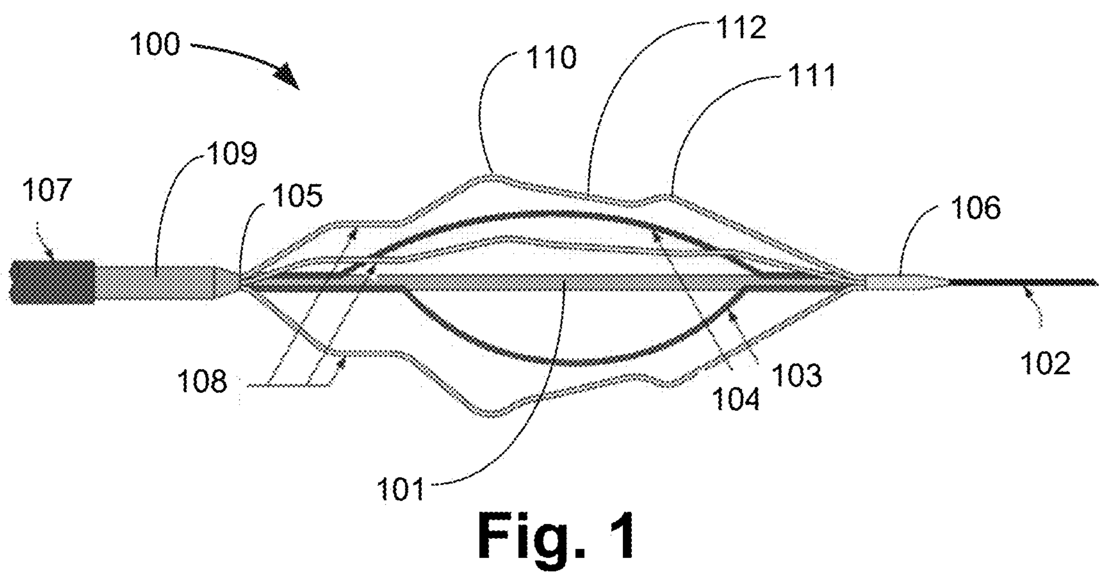
FIG. 1 depicts a cutter according to an embodiment of the present disclosure.

FIG. 1 depicts a cutter 100 according to an embodiment of the present disclosure. The cutter 100 comprises a central catheter 101 that passes over a central wire 102 to travel to a patient's heart (not shown). The cutter 100 comprises one or more cutting wires 103 and 104. The illustrated embodiment depicts two cutting wires 103 and 104. In other embodiments of the cutter 100, more or fewer cutting wires are employed.

The cutting wires 103 and 104 extend from the central catheter 101 near a distal end 105 and then re-attach to the catheter before the distal tip 106. An outer sheath 107 covers the cutting wires 103 and 104 and the central catheter 101 while the cutter 100 travels through the patient's vasculature to the heart. When the cutter 100 is in the proper position (as further discussed herein), the sheath 107 is retracted to expose the wires 103 and 104.

Each of the cutting wires 103 and 104 comprises a cutting surface (not shown). The cutting surface is an abrasive surface that may be diamond, metal, or other material configured to cut into valve tissue when the wires 103 and 104 are rotated at a high speed. In one embodiment, the wires 103 and 104 rotate at a high speed. The cutting wires 103 and 104 bow outward from the central catheter 101 when pressure is applied to the proximal end (not shown) of the catheter.

The cutter 100 further comprises three guidewires 108 which extend from the central catheter 101 between the distal end 105 and distal tip 106 of the catheter 101, in the same area, but radially outwardly, from the cutting wires 103 and 104. Like the cutting wires 103 and 104 discussed above, the guidewires 108 are covered by the outer sheath 107 until the outer sheath 107 is retracted to deploy the guidewires.

Proximal ends of the guidewires 108 are attached to a middle catheter 109 that slides over the central catheter 101. The middle catheter 109 controls the expansion and retraction of the three guidewires 108. This control is done by advancing or retracting the middle catheter 109.

Figure 2:
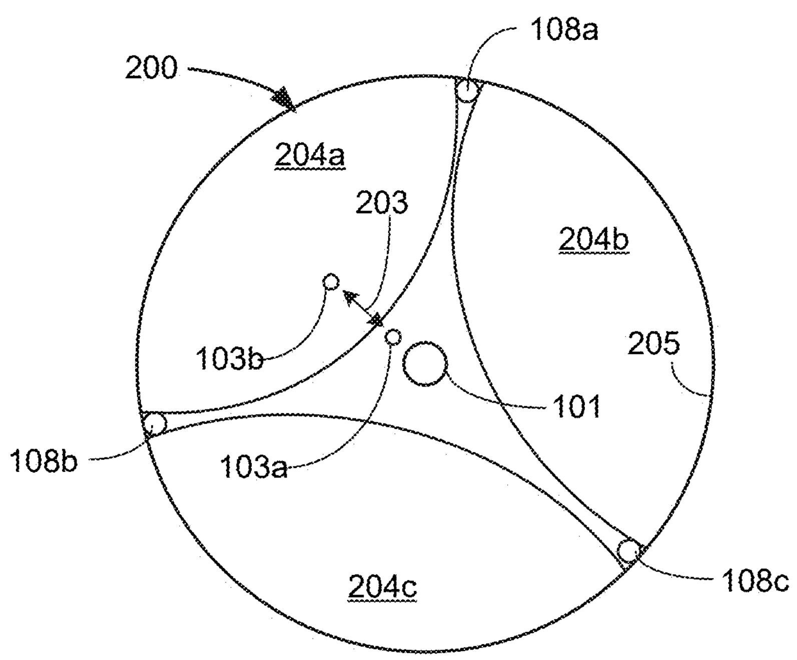
FIG. 2 depicts a cross-sectional representation of the aortic valve cutter of FIG. 1 being used to cut an aortic valve.

The three guidewires 108 fit into the valve leaflet commissures when the guidewires are deployed, as illustrated in FIG. 2. The guidewires 108 serve to center the cutter 100 within the cardiac valve. The guidewires 108 are configured to anchor the cutter 100 vertically in the valve as well. In this regard, the guidewires 108 each comprise a central protrusion 110 and a distal protrusion 111, with a central valley 112 in between.

In one embodiment of the cutter 100, a proximal part of the cutting wires is housed in the wall of the middle catheter 109. Lumens where these wires exit the distal end of the catheter are positioned between the commissure guidewires. The cutting wires 103 and 104 are free-floating in these lumens. Therefore, when the middle catheter 109 is advanced and retracted to control the deployment of the commissural guidewires, the cutting wires' positions are not altered.

The sheath 107 is an outer layer over the middle catheter 109. The sheath 107 extends from the distal tip 106 proximally to just before the handle (not shown) of the cutter 100. When the sheath 107 is retracted towards the handle, the guidewires and cutting segment are exposed and can be deployed as illustrated in FIG. 1. When the guidewires 108 and cutting wires 103 and 104 are retracted, the sheath may be advanced to recapture the cutting wires 103 and 104 and guidewires 108. The distal end of the sheath 107 may contain a sharp edge (not shown) on the distal edge. The sharp edge is provided to help free the cutter from any attached valve leaflet material if needed.

A control handle (not shown) on the cutter 100 has a sliding tab (not shown) for advancing and retracting the middle catheter for the control of the guidewires 108. The handle contains individual control tabs (not shown) for advancing (or bowing) each of the cutting wires. The cutting wires 103 and 104 exit the handle to attach to a motor (not shown) for rotation in some embodiments. In other embodiments, the cutter 100 may contain a motor within the handle.

The handle also has a control tab for advancing and retracting the middle catheter 109 that controls the commissural guidewires 108.

FIG. 2 depicts a cross-sectional representation of the aortic valve cutter 100 of FIG. 1 being used to cut a stenosed aortic valve. To use the cutter 100, the cutter 100 is advanced transfemorally through the patient's aorta (not shown) and across the aortic valve 200, such that the tip of the cutter 100 has entered the left ventricular cavity (not shown). The sheath is withdrawn to expose the guidewires 108*a*, 108*b* and 108*c*, and the middle catheter 109 (FIG. 1) is advanced to deploy the guidewires 108*a*, 108*b*, and 108*c*. The cutter 100 is positioned such that the guidewires 108*a*, 108*b*, and 108*c* are between adjacent valve leaflets, against the interior wall 205 of the aortic valve 200. In the illustrated embodiment, the guidewire 108*a* is between leaflet 204*a* and leaflet 204*b*, the guidewire 108*b* is between leaflet 204*a* and leaflet 204*c*, and the guidewire 108*c* is between leaflet 204*b* and 204*c*. In this position, the cutter 100 is properly centered within the aortic valve 200, with the central catheter essentially centered within the valve 200.

The cutting wire 103 (FIG. 1) is illustrated in a starting position as 103*a* in FIG. 2. In this position, the cutting wire 103*a* is close to the central catheter 101 and adjacent to the leaflet 204*a*. (Note that in FIG. 2, the cutting wire 104 is not illustrated.) In operation of the cutter 100, the user may start the motor (not shown) to start rotation of the cutting wire 103*a*, and may then advance the cutting wire 103*a* outwardly radially until the cutting wire 103*a* begins to cut the leaflet 204*a* along a cutting path 203. The user may advance the cutting wire until it reaches the desired final position, illustrated as 103*b*, having sufficiently cut the leaflet 204*a* as desired by the user.

In a similar manner, the other leaflets 204*b* and 204*c* may be cut. Some embodiments of the cutter comprise three cutting wires, one oriented to cut each leaflet.

Figure 3:
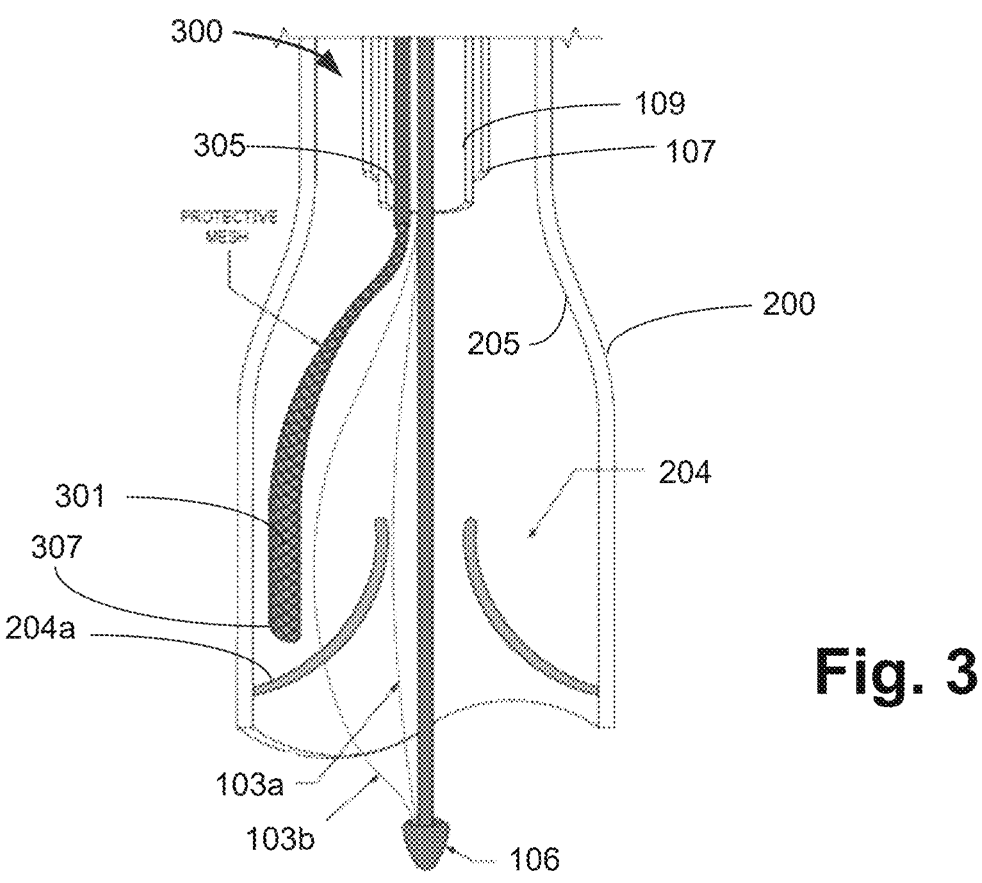
FIG. 3 depicts another embodiment of a cutter according to the present disclosure.

FIG. 3 depicts another embodiment of a cutter 300 according to the present disclosure. In this embodiment, the cutter 300 comprises a deflecting shield 301 positioned between the aortic wall 205 and the aortic side of the valve leaflet 204*a*. The purpose of the shield 301 is to prevent the cutting wire 103 (illustrated in starting position as 103*a* and in "final" position as 103*b*) from cutting into the aortic root or aortic sinus wall.

Figure 5:
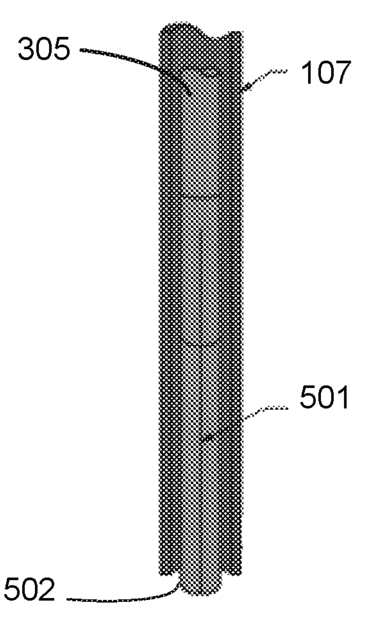
FIG. 5 depicts the shield catheter of FIG. 3 in an undeployed configuration.
Figure 6:
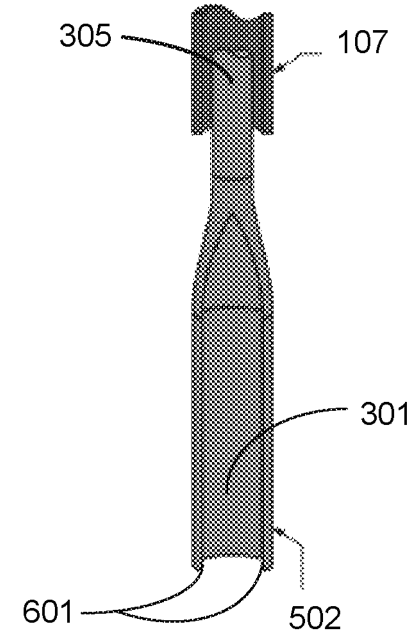
FIG. 6 depicts the shield catheter of FIG. 5 in a deployed configuration.
Figure 7:
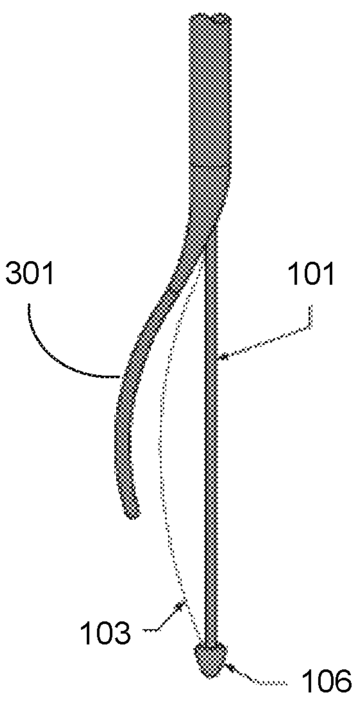
FIG. 7 is a side view of the shield catheter of FIG. 6, showing the shield in conjunction with the cutting wire and central catheter.

In the illustrated embodiment, the shield 301 is supported by a third catheter 305 (also referred to herein as the "shield catheter 305") positioned between the middle guidewire control catheter 109 and the outer (recapture) sheath 107. A distal end 307 of the catheter 305 has a nitinol tube with a longitudinal slit (as illustrated in FIG. 5). When the catheter 305 is extended out from under the outer sheath 107, the distal nitinol segment opens into a generally flat shape. This distal segment opens up the long vertical slit and then forms two generally flat or arc-shaped wings (as illustrated in FIG. 6). The nitinol segment bends out from the central axis of the cutter as well (as illustrated in FIG. 7). The outward bend allows positioning of the flared, distal segment that forms the shield 301 between the aortic wall and the valve leaflet.

The shield 301 serves as a protective barrier or shield between the cutting wire 103 and the aortic wall 205. When the outer sheath 107 is pulled back and the shield 301 is pushed forward, the shield 301 slides between the valve leaflet 204*a* and the Sinus of Valsalva portion of the aortic wall 205.

When the middle catheter 109 is pulled back and the outer sheath 107 is advanced, the distal nitinol tube leaflets will fold back around the middle catheter, as illustrated in FIGS. 5-8. Markers (not shown) on the proximal end of the catheter will show what cutting wire the shield 301 is aligned with. The position of the shield 301 can be confirmed radiographically as well.

Figure 4:
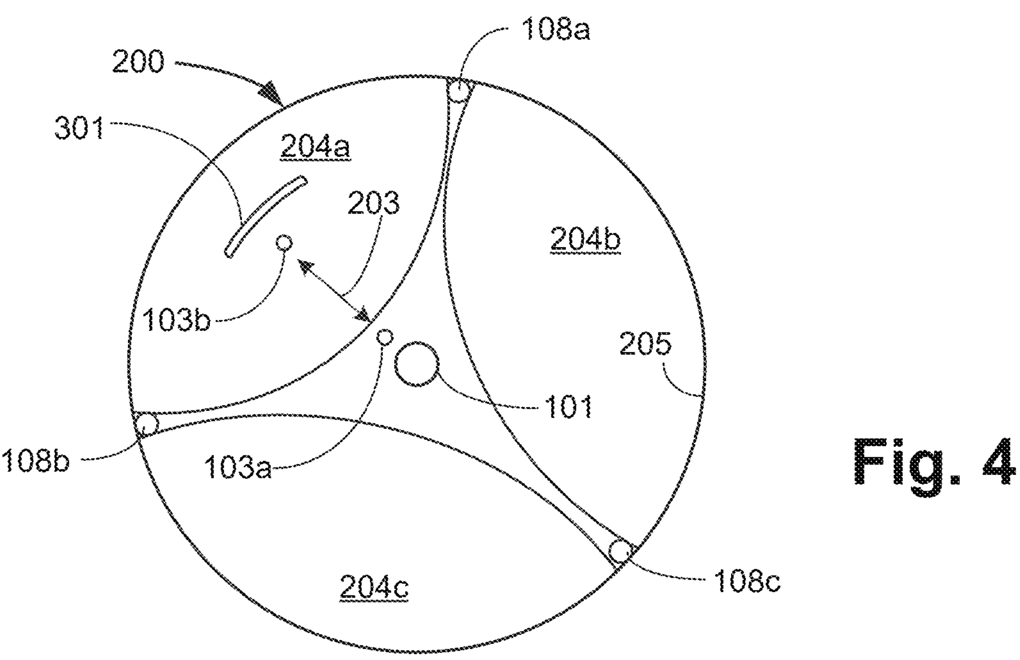
FIG. 4 is a cross-sectional depiction of the cutter of FIG. 3.

FIG. 4 is a cross-sectional depiction of the cutter 300 of FIG. 3, showing the shield 301 between the cutting wire 103*b* (in its outwardmost orientation) and the aortic wall 205.

FIG. 5 depicts the shield catheter 305 of FIG. 3 in an undeployed configuration. The shield catheter 305 is formed from nitinol tubing in one embodiment. As shown in FIG. 5, when the sheath 107 is unretracted, the shield catheter 305 is generally cylindrical in the illustrated embodiment. A vertical slit 501 is disposed in the distal end 502 of the shield catheter 305.

FIG. 6 depicts the shield catheter 305 of FIG. 5 in a deployed configuration, i.e., with the sheath 107 retracted. In this configuration, the distal end 502 opens up due to the vertical slit 501 (FIG. 5), and the "wings" 601 of the distal end flare open to form the shield 301.

FIG. 7 is a side view of the shield catheter 305 of FIG. 6, showing the shield 301 in conjunction with the cutting wire 103 and central catheter 101. As illustrated, the shield 301 bows outwardly from the central catheter 101 when the shield is deployed, i.e., when the sheath 107 (FIG. 6) is retracted.

Figure 8:
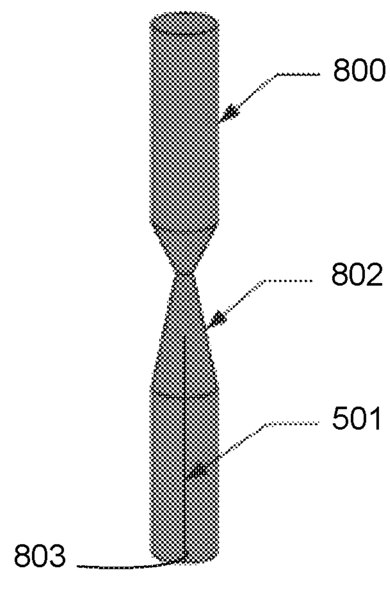
FIG. 8 is an alternative embodiment of a shield catheter 800.

FIG. 8 is an alternative embodiment of a shield catheter 800. The shield catheter 800 is similar to the shield catheter 305 of FIG. 5, except that the tube 8008022 has a conically tapered segment 802 near the distal end 803 as illustrated. The conical tapered segment 802 can make recapture of the shield catheter by the sheath 107 easier, when the sheath is advanced prior to removal of the cutter from the patient.

In another embodiment of the device, the valve leaflet cutting will be done with an electrified wire instead of the rotating or reciprocating diamond wire. A dextrose flush solution may be applied through one of the wire delivery tubes. Aspiration may be possible through the other wire delivery tube. The delivery tubes may be polyimide or other composition. These tubes house the cutting wire down through the shaft of the cutter to the distal tip and then back again to the control handle.

This disclosure may be provided in other specific forms and embodiments without departing from the essential characteristics as described herein. The embodiments described are to be considered in all aspects as illustrative only and not restrictive in any manner.

What is claimed is:

1. A cutting device comprising:

a central catheter adapted to receive a central guide wire, the central guide wire configured to pass the cutting device into a patient's heart;

one or more high speed rotatable or reciprocating cutting wires disposed between the central catheter and a retractable outer sheath;

a plurality of guidewires disposed between the central catheter and the retractable outer sheath, distal ends of each of the plurality of guidewires affixed to a distal tip of the cutting device, the plurality of guidewires configured to center the cutting device within the patient's aortic valve when the guidewires are deployed, each of the plurality of guidewires comprising a central protrusion, a distal protrusion, and a central valley between the central and distal protrusions when the guidewires are deployed a middle catheter affixed to a proximal end of each of the plurality of guidewires, such that advancing the middle catheter when the outer sheath is retracted deploys the plurality of guidewires;

a shield deployable between the one or more cutting wires and an outer wall of the patient's aorta, the shield extending from a shield catheter, the shield catheter disposed between the middle catheter and the outer sheath, the shield catheter comprising a vertical slit near its distal end, distal edges of the vertical slit configured to deploy to form the shield when the sheath is retracted.

2. The cutting device of claim 1, wherein the plurality of guidewires comprises three guidewires, each guidewire configured to fit between adjacent commissures of the aortic valve leaflets.

3. The cutting device of claim 2, wherein the outer sheath that covers the guidewires until the outer sheath is retracted and the guidewires are deployed.

4. The cutting device of claim 1, wherein each of the one or more cutting wires comprises an abrasive cutting surface configured to cut valve tissue when the wire is rotating.

5. The cutting device of claim 4, wherein the abrasive cutting surface comprises a diamond coating.

6. A cutting device comprising:

a central catheter adapted to receive a central guide wire, the central guide wire configured to pass the cutting device into a patient's heart;

one or more high speed rotatable or reciprocating cutting wires disposed between the central catheter and a retractable outer sheath;

a plurality of guidewires configured to center the cutting device within the patient's aortic valve when the guidewires are deployed, each of the plurality of guidewires comprising a central protrusion, a distal protrusion, and a central valley between the central and distal protrusions when the guidewires are deployed a middle catheter affixed to a proximal end of each of the plurality of guidewires, such that advancing the middle catheter when the outer sheath is retracted deploys the plurality of guidewires;

a shield deployable between the one or more cutting wires and an outer wall of the patient's aorta, the shield extending from a shield catheter, the shield catheter disposed between the middle catheter and the outer sheath, the shield catheter comprising a vertical slit near its distal end, distal edges of the vertical slit configured to deploy to form the shield when the sheath is retracted.

7. The cutting device of claim 6, distal ends of each of the plurality of guidewires affixed to a distal tip of the cutting device.

8. The cutting device of claim 7, wherein the plurality of guidewires comprises three guidewires, each guidewire configured to fit between adjacent commissures of the aortic valve leaflets.

9. The cutting device of claim 8, further an outer sheath covers the plurality of guidewires until the outer sheath is retracted and the plurality of guidewires are deployed.

10. The cutting device of claim 6, wherein each of the one or more cutting wires comprises an abrasive cutting surface configured to cut valve tissue when the wire is rotating.

11. The cutting device of claim 10, wherein the abrasive cutting surface comprises a diamond coating.

* * * * *